US010936788B2

United States Patent
Kobayashi et al.

(10) Patent No.: US 10,936,788 B2
(45) Date of Patent: Mar. 2, 2021

(54) DISPLAY CONTROL SYSTEM AND DISPLAY CONTROL METHOD

(71) Applicant: OLYMPUS CORPORATION, Hachioji (JP)

(72) Inventors: Mina Kobayashi, Tokyo (JP); Toshiyuki Hattori, Tokyo (JP); Naohiro Ariga, Tokyo (JP); Ayumu Sakurai, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/926,770

(22) Filed: Mar. 20, 2018

(65) Prior Publication Data

US 2018/0276183 A1 Sep. 27, 2018

(30) Foreign Application Priority Data

Mar. 24, 2017 (JP) .............................. JP2017-059183

(51) Int. Cl.
*G06F 17/00* (2019.01)
*G06F 40/106* (2020.01)
(Continued)

(52) U.S. Cl.
CPC ............ *G06F 40/106* (2020.01); *G06T 11/60* (2013.01); *H04L 67/02* (2013.01); *H04L 67/32* (2013.01); *H04L 67/36* (2013.01)

(58) Field of Classification Search
CPC ......... G06T 2207/30024; G06T 7/0012; G06T 11/60; G06F 40/106; G06F 3/1454;
(Continued)

(56) References Cited

U.S. PATENT DOCUMENTS

| 2005/0051723 A1* | 3/2005 | Neagle .................. C12M 41/14 250/306 |
| 2007/0058054 A1* | 3/2007 | Kagayama ......... G01N 21/6458 348/231.99 |
| 2007/0064101 A1* | 3/2007 | Hasegawa ............ G02B 21/367 348/79 |

FOREIGN PATENT DOCUMENTS

| JP | 2005234435 A | 9/2005 |
| JP | 2009042462 A | 2/2009 |

OTHER PUBLICATIONS

Chinese Office Action (and English translation thereof) dated Jun. 18, 2020, issued in counterpart Chinese Application No. 201810192718.3.

(Continued)

*Primary Examiner* — Andrew T McIntosh
(74) *Attorney, Agent, or Firm* — Holtz, Holtz & Volek PC

(57) ABSTRACT

A display control system includes an image data generation device that generates a plurality of pieces of image data, a storage device that stores the plurality of pieces of image data and a plurality of pieces of position data of holding units, and a display data generation device that generates display data on the basis of the plurality of pieces of image data and position data. The display data is data for aligning and displaying in a fixed direction a plurality of pieces of sample information that includes at least either a plurality of images or a plurality of analysis results, and data that is a result of laying out first sample information and first position information in such a manner that a display device displays the first sample information and the first position information representing a position of a first holding unit corresponding to the first sample information.

20 Claims, 12 Drawing Sheets

(51) Int. Cl.
*H04L 29/08* (2006.01)
*G06T 11/60* (2006.01)

(58) Field of Classification Search
CPC ......... H04L 67/36; H04L 67/02; H04L 67/32; C12M 41/36; H04N 7/18
See application file for complete search history.

(56) References Cited

OTHER PUBLICATIONS

Chinese Office Action (and English language translation thereof) dated Nov. 27, 2019 issued in counterpart Chinese Application No. 201810192718.3.

* cited by examiner

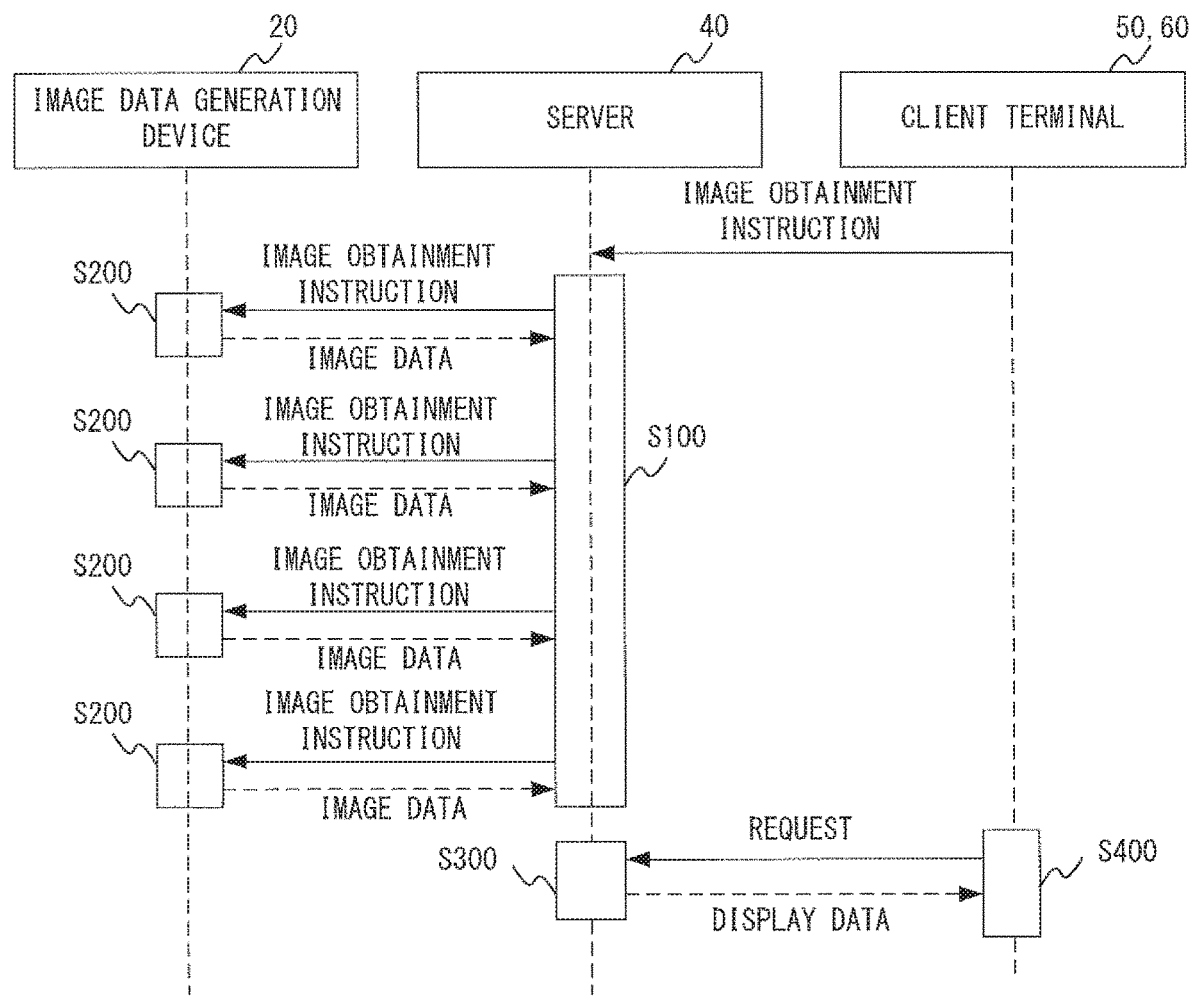
F I G. 3

DISPLAY CONTROL SYSTEM AND DISPLAY CONTROL METHOD

CROSS REFERENCE TO RELATED APPLICATIONS

This application is based upon and claims the benefit of priority from prior Japanese Patent Application No. 2017-059183, filed Mar. 24, 2017, the entire contents of which are incorporated herein by this reference.

BACKGROUND OF THE INVENTION

Field of the Invention

The present invention is related to a display control system and a display control method.

Description of the Related Art

In the field of biochemistry, an operation is often conducted in which a microscope etc. is used for repeatedly picking up images of biological samples that are being cultured and for monitoring the growth of the biological samples. Biological samples are usually held in a container such as a microplate. It is not rare for a plurality of biological samples to be cultured in parallel in regions that are partitioned in a container, and thus there is a demand for a technique of observing or monitoring a plurality of biological samples highly efficiently.

Such a technique is proposed in for example Japanese Laid-open Patent Publication No. 2005-234435. Japanese Laid-open Patent Publication No. 2005-234435 describes a technique of displaying an image of a biological sample in which a change has been detected, together with change detection information indicating the detection of the change, the change having occurred with the passage of time.

There is a demand for further improvement in display control techniques of realizing efficient observation or monitoring partly because of the spread of mobile terminals in recent years or because of other factors.

SUMMARY OF THE INVENTION

A display control system according to an aspect of the invention includes an image data generation device configured to pick up images of a plurality of samples held in a plurality of holding units so as to generate a plurality of pieces of image data, a storage device configured to store the plurality of pieces of image data generated by the image data generation device and a plurality of pieces of position data of holding units corresponding to the plurality of pieces of image data, each of the plurality of pieces of image data being associated with a piece of position data among the plurality of pieces of position data, and a display data generation device configured to generate display data on the basis of the plurality of pieces of image data stored in the storage device and the plurality of pieces of position data stored in association with the plurality of pieces of image data. The display data is data for aligning and displaying, in a fixed direction, a plurality of pieces of sample information that include at least either a plurality of images representing the plurality of samples or a plurality of analysis results on the plurality of pieces of image data. And, the display data is a result of laying out a first piece of sample information and a first piece of position information in such a manner that when a display device is displaying the first piece of sample information from among the plurality of pieces of sample information on the basis of the display data, the first piece of position information representing a position of a first holding unit corresponding to the first piece of sample information from among the plurality of holding units is displayed on the display device.

A display control method according to an aspect of the present invention is a display control method performed in a display control system. The display control method includes picking up, by using an image data generation device included in the display control system, images of a plurality of samples held in a plurality of holding units so as to generate a plurality of pieces of image data, storing, by using a storage device included in the display control system, the plurality of pieces of image data generated by the image data generation device and a plurality of pieces of position data of holding units corresponding to the plurality of pieces of image data, each of the plurality of pieces of image data being associated with a piece of position data among the plurality of pieces of position data, and generating, by using a display data generation device included in the display control system, display data on the basis of the plurality of pieces of image data stored in the storage device and the plurality of pieces of position data stored in association with the plurality of pieces of image data. The display data is data for aligning and displaying, in a fixed direction, a plurality of pieces of sample information that include at least either a plurality of images representing the plurality of samples or a plurality of analysis results on the plurality of pieces of image data. And, the display data is a result of laying out a first piece of sample information and a first piece of position information in such a manner that when a display device is displaying the first piece of sample information from among the plurality of pieces of sample information on the basis of the display data, the first piece of position information representing a position of a first holding unit corresponding to the first piece of sample information from among the plurality of holding units is displayed on the display device.

BRIEF DESCRIPTION OF THE DRAWINGS

The present invention will be more apparent from the following detailed description when the accompanying drawings are referenced.

FIG. 3 is a sequence diagram exemplifying processes in respective devices and communications of data between the devices;

DESCRIPTION OF THE EMBODIMENTS

Figure 1:
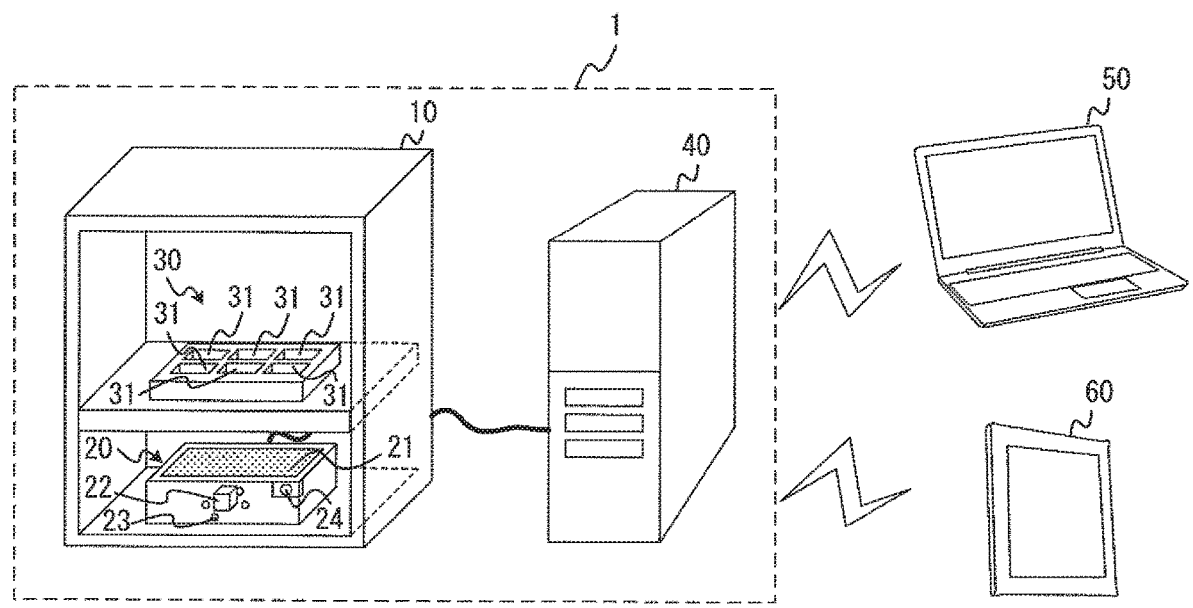
FIG. 1 exemplifies a configuration of a display control system 1.
Figure 2:
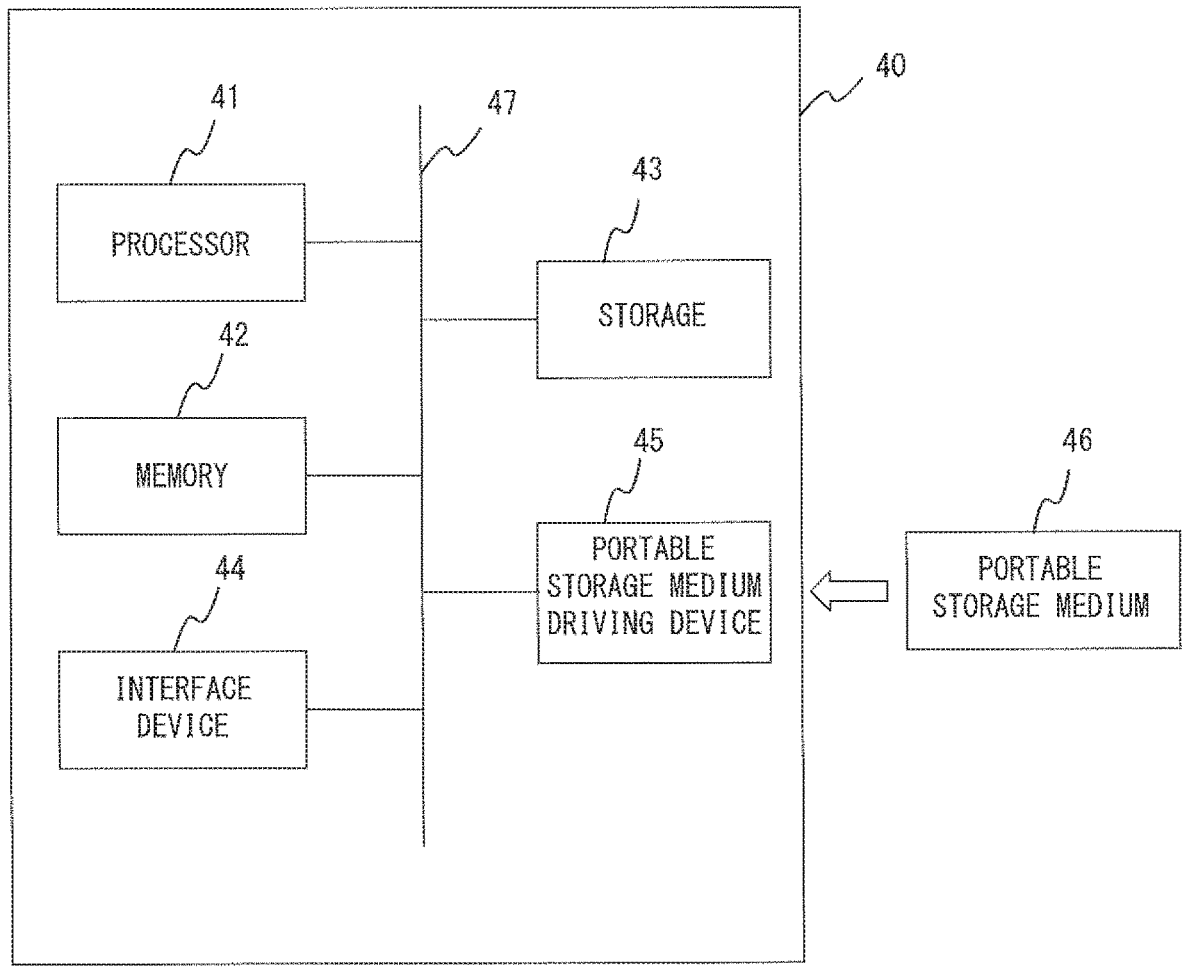
FIG. 2 exemplifies a hardware configuration of a server 40.

FIG. 1 exemplifies a configuration of a display control system 1 according to an embodiment. FIG. 2 exemplifies a hardware configuration of a server 40. The display control system 1 is a system that assists observation or monitoring of a plurality of samples that are held in a microplate 30 etc. Target samples are for example biological samples such as cultured cells. The user of the display control system 1 uses a client terminal such as a notebook computer 50, a tablet computer 60, a smartphone, etc. to access the display control system 1 through at least one of the wireless and wired communications. Thereby, the user can observe or monitor the biological samples. Note that a client terminal is provided with for example a display device such as a liquid crystal display device. The display device may be a touch panel display device.

The display control system 1 is provided with an image data generation device 20 that generates image data, and a server 40, which is a display data generation device that generates display data on the basis of at least image data generated by the image data generation device 20. The image data generation device 20 and the server 40 are connected via for example a wired cable such as a Universal Serial Bus (USB) cable etc. It is sufficient if the image data generation device 20 and the server 40 are configured to allow mutual data communicates, and they may be connected to allow not only wired communications but also wireless communications.

The image data generation device 20 is set in for example an incubator 10 in which the microplate 30 is arranged, as illustrated in FIG. 1. The microplate 30 has a plurality of wells 31, each of which is a holding unit, and each of the wells 31 holds a sample. The plurality of samples held in the plurality of wells 31 may be of the same type or may be of different types. The incubator 10 is a device that maintains or controls the culturing environment, and is an incubator that cultures a plurality of samples held in the microplate 30. FIG. 1 illustrates an example in which the microplate 30 is arranged apart from the image data generation device 20 by being mounted on the supporting plate in the incubator 10. However, the microplate 30 may be mounted directly on the upper plane of the image data generation device 20 without having a supporting plate between them.

The image data generation device 20 is provided with an image sensor 22, a plurality of illumination LED light sources 23 arranged around the image sensor 22, and a temperature sensor 24. The image sensor 22 is for example a CCD (Charge-CoupledDevice) image sensor, a CMOS (Complementary MOS) image sensor, etc. The image sensor 22 and the plurality of illumination LED light sources 23 are provided in such a manner that they can move freely under an image-pick-up area 21. The temperature sensor 24 is a sensor that measures the temperature inside the incubator 10. Also, the image data generation device 20 may be provided with a different sensor that measures the environment inside the incubator 10.

The server 40 is for example a standard computer. As illustrated in FIG. 2, the server 40 is provided with a processor 41, a memory 42, a storage 43, an interface device 44 and a portable storage medium driving device 45 into which a portable storage medium 46 is inserted. They are connected to each other via a bus 47.

The processor 41 is for example a CPU (Central Processing Unit), an MPU (Micro Processing Unit), a DSP (Digital Signal Processor), etc., and executes a program so as to perform the programmed process. The memory 42 is for example a RAM (Random Access Memory). The memory 42 temporarily stores a program or data that is stored in the storage 43 or the portable storage medium 46 when the program is to be executed.

The storage 43 is for example a hard disk or a flash memory, and is used mainly for storing various types of data or a program. The interface device 44 is a circuit that communicates a signal to a device (for example, the image data generation device 20, the notebook computer 50, the tablet computer 60, etc.) other than the server 40. The portable storage medium driving device 45 accommodates the portable storage medium 46 such as an optical disk, a compact flash (registered trademark), etc. The portable storage medium 46 has a function of assisting the storage 43. The storage 43 and the portable storage medium 46 are respectively examples of a non-transitory computer-readable storage medium that has stored a program.

Note that the configuration illustrated in FIG. 2 is an example of a hardware configuration of the server 40. And the server 40 is not limited to this configuration. The server 40 may not be a general-purpose device, and may be a dedicated device. The server 40 may be provided with an electric circuit such as an ASIC (Application Specific Integrated Circuit), an FPGA (Field Programmable Gate Array), etc. instead of or in addition to a processor that executes a program. The processes that will be described later may be executed by such an electric circuit.

The display control system 1 having the above configuration mainly performs the two processes that will be described below. The first is an image data storage process, and the second is a display data output process. In the present embodiment, the image data storage process is performed by the image data generation device 20 and the server 40, and the display data output process is performed by the server 40.

In the image data storage process, the server 40 first outputs an image obtainment instruction to the image data generation device 20. In this process, the server 40 outputs, to the image data generation device 20, an instruction including for example information for identifying the plurality of wells 31 that hold the plurality of samples, which are image pick-up targets.

Next, in accordance with the instruction from the server 40, the image data generation device 20 picks up images of the plurality of samples held in the plurality of wells 31, and generates a plurality of pieces of image data so as to output them to the server 40. In more detail, the image data generation device 20 picks up images of the plurality of samples that are respectively held in the plurality of wells 31, generates a plurality of pieces of image data, each of which is image data of its corresponding one of the plurality of samples, and outputs the pieces of image data to the server 40.

Specifically, the image data generation device 20 first moves the image sensor 22 and the plurality of illumination LED light sources 23 to the position below a sample that is the first image pick-up target from among a plurality of samples held in the microplate 30, and picks up an image of the sample that is the first image pick-up target. Thereafter, the image data generation device 20 moves the image sensor 22 and the plurality of illumination LED light sources 23 to the position below a sample that is the second image pick-up target, and picks up an image of the sample that is the second image pick-up target. By repeating this process on all the samples that are the image pick-up targets, a plurality of pieces of image data are generated. Note that the image data generation device 20 may also output, to the server 40 and in addition to image data, data on the environment of the incubator 10 such as temperature data etc. output from the temperature sensor 24 (which will hereinafter be referred to as environment data).

Lastly, the server 40 stores the pieces of the image data and the pieces of position data of the wells 31 corresponding to the pieces of image data in association with each other. In this example, the storage 43, which is an example of a storage device included in the server 40, stores each of a plurality of pieces of image data having been generated by the image data generation device 20 and a plurality of pieces of position data of the wells 31 corresponding to the plurality of pieces of image data. Each of the plurality of pieces of image data is associated with a piece of position data among the plurality of pieces of position data. Note that the wells 31 corresponding to pieces of image data are the wells 31 holding samples represented in images that are displayed on the basis of those pieces of image data.

Also, when the server 40 has received environment data of the incubator 10 from the image data generation device 20, the storage 43 may store the environment data in association with the image data and the position data.

In the display data output process, the server 40 generates display data on the basis of a plurality of pieces of image data and a plurality of pieces of position data stored in association with the plurality of pieces of image data, the plurality of pieces of image data and a plurality of pieces of position data being stored in the storage 43. In this process, in response to for example a request (HTTP request) from the client terminal, the server 40 generates a web page that is display data. And the server 40 transmits a response including the web page (i.e., an HTTP response having the web page embedded in the body) to the client terminal. Display data generated by the server 40 will be described later in detail.

Hereinafter, by referring to FIG. 3 through FIG. 8, specific explanations will be given for processes performed in the display control system 1 and the client terminal of the display control system 1. In this example, explanations will be given for an example in which the display control system 1 is a web system and a time-lapse control process is performed for generating and outputting display data on the basis of image data stored in the storage 43.

FIG. 3 is a sequence diagram exemplifying processes in the respective devices and communications of data between the devices, and illustrates an example of display control performed by the display control system 1. As illustrated in FIG. 3, an image obtainment instruction instructing the start of the execution of a time-lapse observation is first transmitted from the client terminal to the server 40, and a time-lapse control process is started in the server 40 in response to the transmission. Then, the server 40 performs a time-lapse control process (step S100), and thereby the image data generation device 20 repeats an image obtainment process during the execution period of the time-lapse control process (step S200). Then, the image obtainment instruction is transmitted from the server 40 to the image data generation device 20, and image data is transmitted from the image data generation device 20 to the server 40.

Thereafter, the server 40 performs a display data output process in response to the request from the client terminal (step S300), and the client terminal that received the display data performs a display process (step S400). Then, the request is transmitted from the client terminal to the server 40, and a response including the display data is transmitted from the server 40 to the client terminal.

Figure 4:
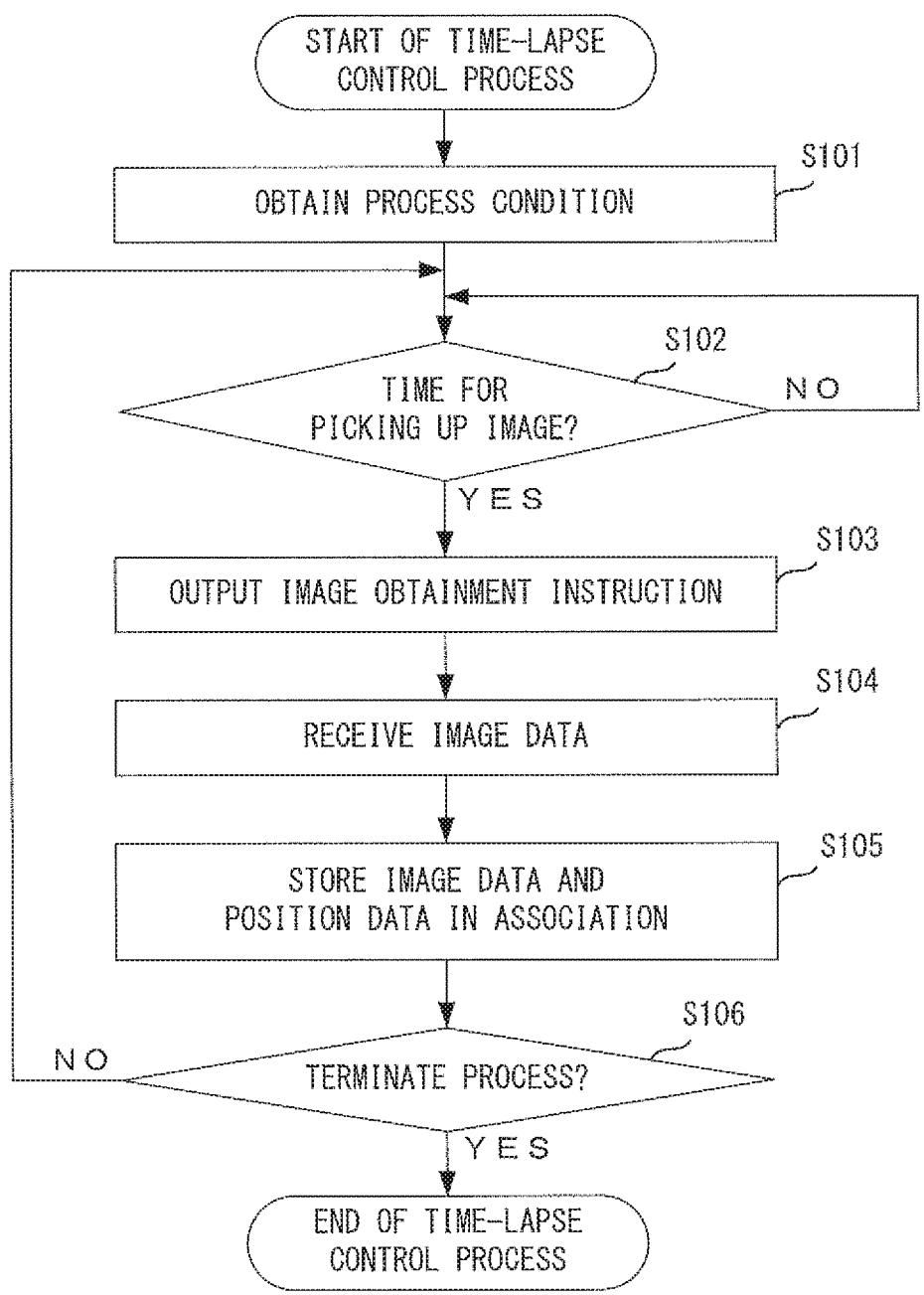
FIG. 4 is a flowchart exemplifying a time-lapse control process.

FIG. 4 is a flowchart exemplifying a time-lapse control process. As illustrated in FIG. 4, when a time-lapse control process is started, the server 40 first obtains a process condition (step S101). In this step, the server 40 obtains a process condition that has been input by using an input device (not illustrated), and stores it in the storage 43. A process condition includes, among others, for example the positions of the plurality of wells 31 included in the microplate 30, the positions of the wells 31 that hold samples as image pick-up targets, the image-pickup-time interval, and the number of times of picking up.

Obtaining the process condition, the server 40 determines whether or not the current time has reached the time for picking up images (step S102). In this step, the server 40 calculates the time for picking up images on the basis of the image-pickup-time interval obtained in step S101. When determining that the current time has reached the time for picking up images, the server 40 outputs an image obtainment instruction to the image data generation device 20 (step S103). The image obtainment instruction includes information for identifying the location of the well 31 that holds a sample as an image pick-up target. Thereby, the image obtainment process illustrated in FIG. 5 is performed by the image data generation device 20.

Thereafter, the server 40 receives a piece of image data from the image data generation device 20 (step S104), and stores the piece of image data and a piece of position data indicating the position of the well 31 that corresponds to that piece of image data in association with each other (step S105). In this example, the server 40 determines the piece of image data received from the image data generation device 20 to be the piece of image data of the sample held in the well 31 at the position specified by the image obtainment instruction, and thereby identifies the position data corresponding to the received piece of image data. Note that when a plurality of samples are specified as image pick-up targets, the server 40 receives a plurality of pieces of image data in step S104, and stores the plurality of pieces of image data and the corresponding pieces of position data in association with each other in step S105.

Lastly, the server 40 determines whether or not to terminate the time-lapse control process (step S106). When the number of times of repeating of the processes between step S102 through step S106 has not reached the number of times of picking up images obtained in step S101, it is determined not to terminate the time-lapse control process, and the processes between step S102 and step S106 are repeated. When the number of times of repeating has reached the number of times of picking up images, the time-lapse control process is terminated.

Figure 5:
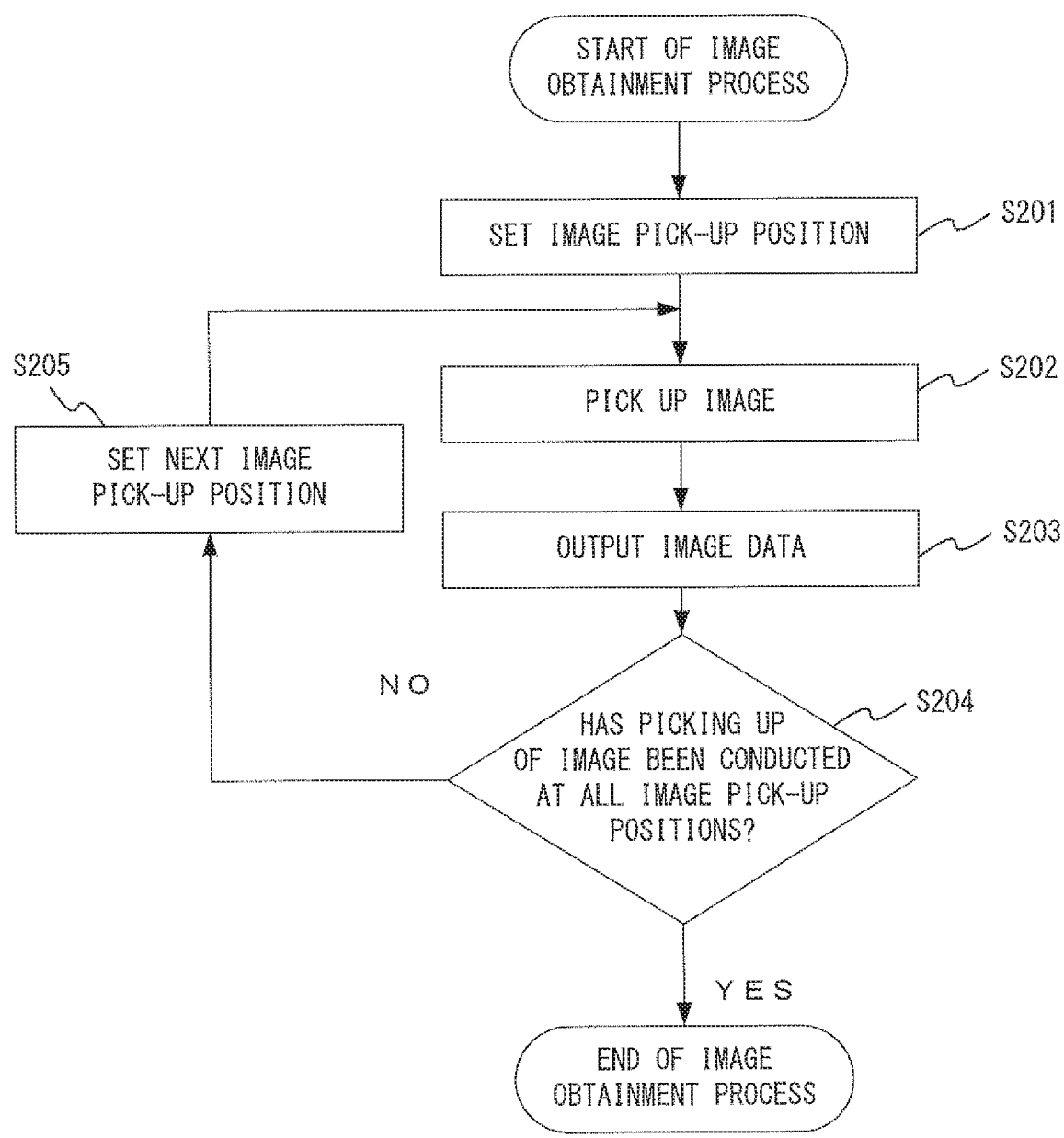
FIG. 5 illustrates a flowchart exemplifying an image obtainment process.

FIG. 5 illustrates a flowchart exemplifying an image obtainment process. As illustrated in FIG. 5, when an image obtainment process is started, the image data generation device 20 first sets an image pick-up position (step S201). In the process, the image data generation device 20 calculates an image pick-up position on the basis of information for identifying the position of the well 31 included in the image obtainment instruction received from the server 40, and moves the image sensor 22 and the plurality of illumination LED light sources 23 to the position in accordance with the image pick-up position.

Next, the image data generation device 20 picks up an image of a sample (step S202), and outputs the generated image data of the sample to the server 40 (step S203).

Thereafter, the image data generation device 20 determines whether or not picking up of an image has been conducted at all image pick-up positions (i.e., the positions of all the wells 31 identified from information included in the image obtainment instruction) (step S204). When it is determined that the picking up of an image has not been conducted at all the image pick-up positions, the server 40 sets a next image pick-up position (step S205), and repeats the processes from step S202 through step S204. When it is determined that the picking up of an image has been conducted at all the image pick-up positions, the server 40 terminates the image obtainment process.

By the display control system 1 performing the time-lapse control process illustrated in FIG. 4 and the image obtainment process illustrated in FIG. 5, at least image data and position data are stored in association with each other in the storage 43 of the server 40. Note that the time-lapse control process illustrated in FIG. 4 and the image obtainment process illustrated in FIG. 5 correspond to the above image data storage process.

Figure 6:
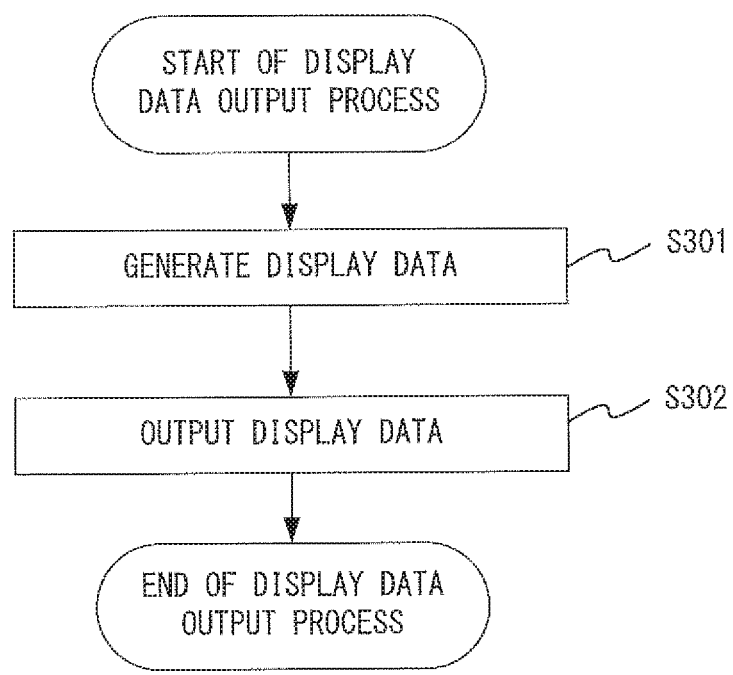
FIG. 6 is a flowchart exemplifying a display data output process.

FIG. 6 is a flowchart exemplifying a display data output process. When receiving a request (HTTP) from a client terminal, the server 40 starts the display data output process illustrated in FIG. 6. First, the server 40 generates display data in accordance with the request (step S301).

A case is assumed for example in which a request specifying, as observation targets, a plurality of samples held in different wells 31 is received. In such a case, the server 40 reads, from the storage 43, a plurality of pieces of image data corresponding to the specified observation targets and a plurality of pieces of position data stored in association with the plurality of pieces of image data, and generates display data on the basis of these pieces of data.

Display data is data for aligning and displaying, in a fixed direction, pieces of information of a plurality of samples specified as observation targets (which will be referred to as sample information). A plurality of pieces of sample information used herein include at least either a plurality of images representing a plurality of samples specified as observation targets or a plurality of image analysis results. In more detail, each of the plurality of images represents a corresponding sample of the plurality of samples specified as the observation targets, and each of the plurality of image analysis results is information, obtained through the image analysis, of a corresponding sample of the plurality of samples specified as the observation targets.

Further, in addition to sample information (images and analysis results), display data includes position information indicating the position of the well 31 of interest. Display data is also data that is a result of laying out a first piece of sample information and a first piece of position information in such a manner that when the display device is displaying the first piece of sample information from among a plurality of pieces of sample information on the basis of the display data, the first piece of position information indicating the position of the well 31 (first well) corresponding to the first piece of sample information from among the plurality of wells 31 is displayed on the display device.

A first piece of position information may be information indicating a relative position of the first well with respect to the plurality of wells 31. In such a case, it is desirable that the first piece of position information include array information that graphically represents the array of the plurality of wells 31 and identification information indicating the position of the first well in that array. It is further desirable that array information include a plurality of figures representing the shapes of the plurality of respective wells 31. The first piece of position information such as this is advantageous in that it permits the position of the well 31 of interest to be known intuitively. It is also advantageous in that it permits the position of the well 31 of interest to be known even when the client terminal (display device) is small, such as in a case when the client terminal is a smartphone. Alternatively, the first piece of position information may include character information indicating the position of the first well in the array of the plurality of wells 31.

Thereafter, the server 40 outputs display data generated in step S301 (step S302), and terminates the display data output process. In the process, the server 40 embeds the display data in the body of an HTTP response so as to transmit it to the client terminal.

Figure 7:
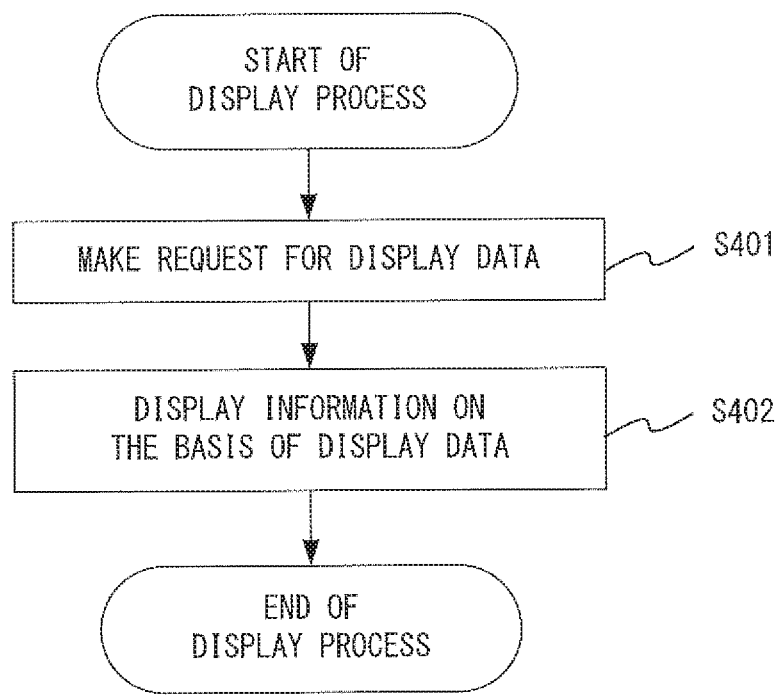
FIG. 7 is a flowchart exemplifying a display process.

FIG. 7 is a flowchart exemplifying a display process. The client terminal first makes a request to the server 40 for display data (step S401). In this process, the client terminal transmits, to the server 40, a request including information that specifies a plurality of samples as observation targets. This request is for example an HTTP request transmitted to the server 40 from a web browser installed in the client terminal.

Thereafter, the client terminal displays the information on the basis of the display data received from the server 40 (step S402). In this process, the client terminal receives display data including a plurality of pieces of sample information on a plurality of specified samples, and displays the information on the display device of the client terminal on the basis of the display data. The display data is for example a web page included in the HTTP response, and the web browser of the client terminal that received the HTTP response displays the web page on the basis of the display data.

Figure 8:
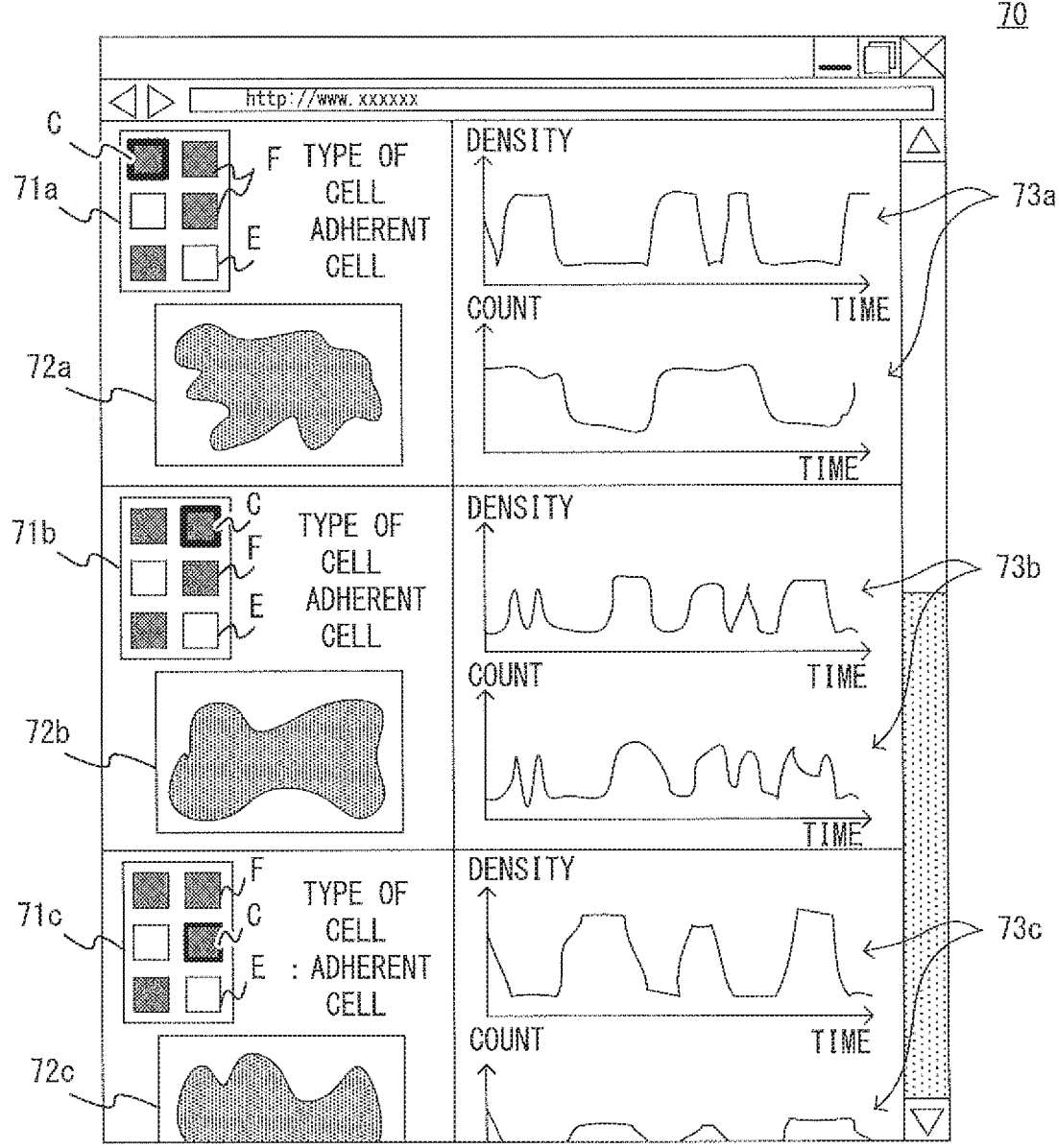
FIG. 8 illustrates an example of a web page that is displayed on the web browser.
Figure 9:
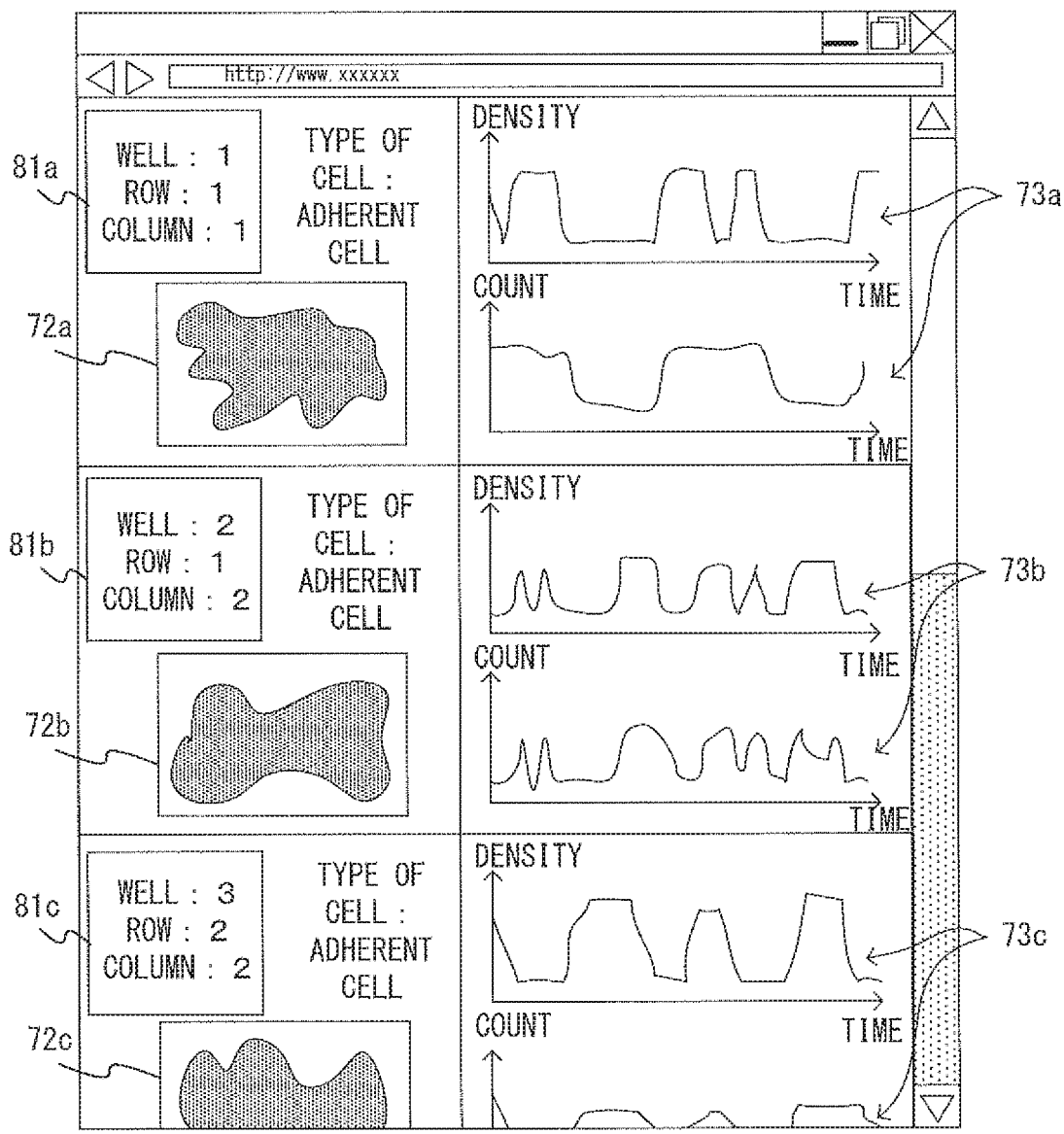
FIG. 9 illustrates another example of a web page that is displayed on the web browser.

FIG. 8 and FIG. 9 exemplify web pages that are displayed on the web browser on the basis of a response from the display control system 1. On a web page 70 illustrated in FIG. 8 and a web page 80 illustrated in FIG. 9, a plurality of pieces of position information that correspond to a plurality of pieces of sample information are aligned in the same direction as a plurality of pieces of sample information, and thereby position information and sample information (image and analysis results) are displayed in a group for each sample.

In this example, a plurality of pieces of position information are pieces of position information 71$a$ through 71$c$ and pieces of position information 81$a$ through 81$c$. A plurality of pieces of sample information are an image 72$a$ and an image analysis result 73$a$, an image 72$b$ and an image analysis result 73$b$, and an image 72$c$ and an image analysis result 73$c$. Also, the images 72$a$ through 72$c$ are for example most recent images of their corresponding samples. Image analysis results 73$a$ through 73$c$ include for example graphs, each calculated through image analyses, showing the densities of adherent cells included in the samples and the time changes of the number of the cells.

The pieces of the position information 71$a$ through 71$c$ included in the web page 70 illustrated in FIG. 8 include array information (six boxes) that graphically represents the array of the plurality of wells 31 in the microplate 30 and identification information C that indicates the position of the well 31 of interest in the array. The array information indicates that six wells 31 exist in the microplate 30, that, among them, four wells 31 represented by the black boxes F dotted with high density hold samples, and that the remaining two wells 31 represented by white boxes E do not hold samples. Note that each of the six boxes included in the array information is a figure that represents the shape of the well 31.

Identification information C included in the position information 71a indicates that the image 72a and the image analysis result 73a displayed closely to the position information 71a are the sample information on the sample held in the well 31 that is located at the upper left position of the microplate 30. Identification information C included in the position information 71b indicates that the image 72b and the image analysis result 73b are the sample information on the sample held in the well 31 that is located at the upper right position of the microplate 30. Identification information C included in the position information 71c indicates that the image 72c and the image analysis result 73c are the sample information on the sample held in the well 31 that is located at the middle right position of the microplate 30.

The pieces of the position information 81a through the position information 81c included in the web page 80 illustrated in FIG. 9 include character information indicating the position of the well 31 of interest in the array of the plurality of wells 31.

The position information 81a indicates that the well 31 of interest is located at the position in the first row and first column and that an image 72a and an image analysis result 73a displayed close to the position information 81a are the sample information on the sample held in the well 31 located at the position of the first row and first column of the array of the microplate 30. The position information 81b indicates that the well 31 of interest is located at the position in the first row and second column and that an image 72b and an image analysis result 73b displayed close to the position information 81b are the sample information on the sample held in the well 31 located at the position of the first row and second column of the array of the microplate 30. The position information 81c indicates that the well 31 of interest is located at the position in the second row and second column and that an image 72c and an image analysis result 73c displayed close to the position information 81c are the sample information on the sample held in the well 31 located at the position of the second row and second column of the array of the microplate 30.

As described above, by the client terminal performing a display process on the basis of display data generated by the display control system 1, a plurality of pieces of sample information are aligned and displayed in a fixed direction. This makes it possible for the user to easily confirm the sample information on an arbitrary biological sample through a scrolling operation even when all of a plurality of pieces of sample information cannot be displayed on a display device at one time.

Further, by aligning a plurality of pieces of position information so that they are in the same direction as a plurality of pieces of sample information in display data generated by the display control system 1, a plurality of pieces of sample information and a plurality of pieces of position information are laid out in such a manner that the display device displays pieces of position information that correspond to pieces of sample information that are being displayed. This makes it always possible for the user to grasp which of the wells 31 the pieces of information of the biological samples being displayed are held in even when pieces of sample information are displayed while being switched frequently through scrolling operations.

Accordingly, the display control system 1 makes it possible for the user to observe or monitor a plurality of biological samples efficiently. In particular, when the display control system 1 is a web system, it is easy to confirm an arbitrary piece of sample information and the piece of position information that corresponds to the piece of sample information by performing a scrolling operation upward and downward on the web browser.

Figure 10:
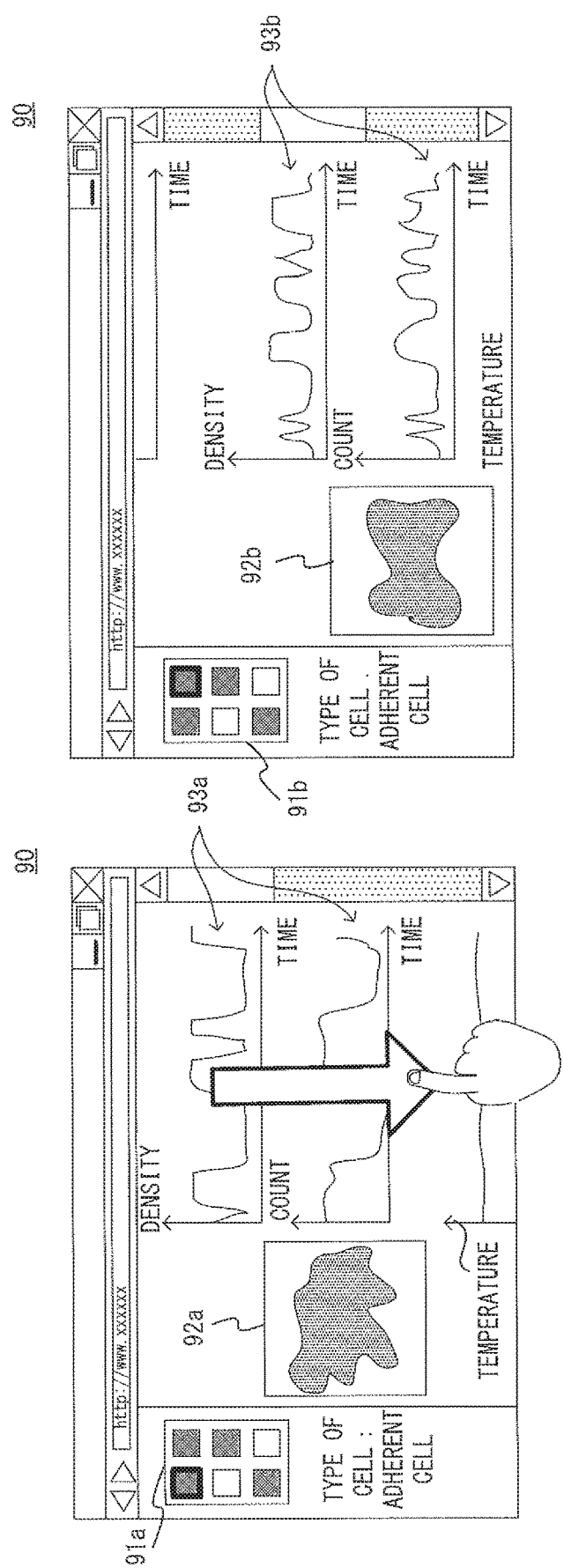
FIG. 10A illustrates still another example of a web page that is displayed on the web browser, and illustrates a state before a scrolling operation.
FIG. 10B illustrates still another example of a web page that is displayed on the web browser, and illustrates a state after a scrolling operation.

FIG. 10A and FIG. 10B illustrate other examples of web pages displayed on the web browser in response to the response from the display control system 1. While FIG. 8 and FIG. 9 illustrate examples in which the display data is for aligning and displaying, in a fixed direction, a plurality of pieces of position information that correspond to a plurality of pieces of sample information and both of the position information and sample information move together through a scrolling operation, a configuration may be employed in which only sample information moves through a scrolling operation with the position information remaining still. The display control system 1 may generate a web page 90 illustrated in FIG. 10A and FIG. 10B instead of the web page illustrated in FIG. 8 or FIG. 9.

The web page 90 illustrated in FIG. 10A and FIG. 10B is similar to the web pages illustrated in FIG. 8 and FIG. 9 in that a plurality of pieces of sample information (image 92a and image analysis result 93a, and image 92b and image analysis result 93b) are aligned and displayed in a fixed direction. This makes it easy to display an arbitrary piece of sample information through a scrolling operation.

The web page 90 illustrated in FIG. 10A and FIG. 10B is different from the web page illustrated in FIG. 8 or FIG. 9 in that the piece of position information corresponding to the piece of sample information that is being displayed is displayed at a fixed position on the browser and that the display of position information is updated in response to switching, through a scrolling operation, of the piece of sample information that is being displayed. Note that FIG. 10A illustrates a state before a scrolling operation, and FIG. 10B illustrates a state after a scrolling operation.

In the web page 90, when the state of the web browser changes, in response to a scrolling operation, from a state in which the sample information (image 92a and image analysis result 93a) of the sample held in the upper left well 31 is displayed to a state in which the sample information (image 92b and image analysis result 93b) of the sample held in the upper right well 31 is displayed, the position information is updated to the position information 91b that represents the upper right well 31 from the position information 91a that represents the upper left well 31.

In the web page 90 illustrated in FIG. 10A and FIG. 10B as well, the position information corresponding to the sample information that is being displayed is displayed on the display device. In particular, because position information is displayed at a fixed position, the user will not lose position information through a scrolling operation. This makes it always possible for the user to grasp which of the wells 31 the piece of information of the biological sample being displayed is held in even when the pieces of sample information are displayed while being switched frequently through scrolling operations. Accordingly, it is made possible to observe or monitor a plurality of biological samples efficiently.

Figure 11:
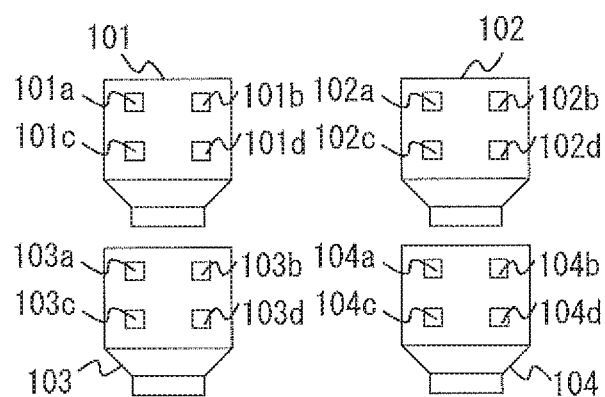
FIG. 11 illustrates an example of a group of containers that hold samples.

While the above example exemplifies the wells 31 provided to the microplate 30 as an example of holding units for holding biological samples, holding units for holding biological samples are not limited to the wells 31. For example, biological samples may be cultured in a state in which they are held in flasks (flasks 101 through 104), as illustrated in FIG. 11. Also, although an example in which an image is obtained at one location for each holding unit was described, images may be picked up at a plurality of locations in one holding unit so as to obtain a plurality of images. FIG. 11 illustrates an example in which images of a sample are picked up at four locations for each flask.

The flask 101 has, as its image pick-up target areas, four locations, from an image pick-up target area 101*a* through an image pick-up target area 101*d*. The flask 102 has, as its image pick-up target areas, four locations, from an image pick-up target area 102*a* through an image pick-up target area 102*d*. The flask 103 has, as its image pick-up target areas, four locations, from an image pick-up target area 103*a* through an image pick-up target area 103*d*. The flask 104 has, as its image pick-up target areas, four locations, from an image pick-up target area 104*a* through an image pick-up target area 104*d*.

Figure 12:
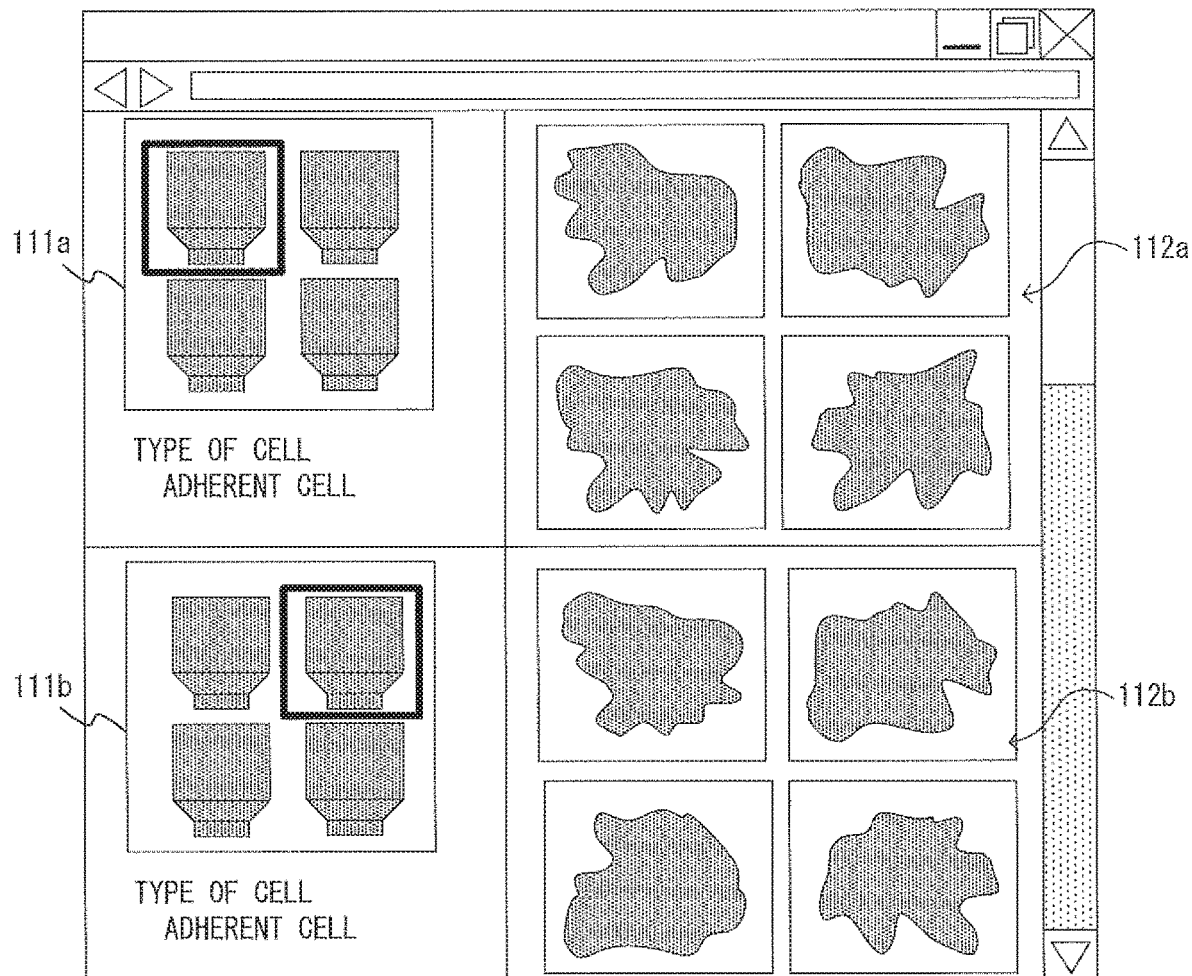
FIG. 12 illustrates still another example of a web page that is displayed on the web browser.

The display control system 1 may employ a configuration in which the image data generation device 20 picks up images of a sample at four locations for each flask, as illustrated in FIG. 11, so as to obtain four images, and the server 40 generates a web page 110 as illustrated in FIG. 12. FIG. 12 illustrates a situation in which a plurality of pieces of position information (position information 111*a* and position information 111*b*) are aligned in the same direction as a plurality of pieces of sample information (image group 112*a* and image group 112*b*) and thereby position information and sample information are displayed in a group for each sample. In this case too, the user can easily confirm an arbitrary piece of sample information and the piece of position information corresponding to the piece of sample information by performing scrolling operations upward and downward on the web browser. Also, it is always possible to grasp which of the flasks the piece of information of the biological sample that is being displayed is held in.

The above embodiments are specific examples for facilitating the understanding of the invention, and the embodiment of the present invention is not limited to them. The display control system and the display control method allow various modifications and changes without departing from the descriptions of the claims.

For example, while timings for analyzing image data have not been specifically mentioned, the server 40 may analyze image data during a time-lapse control process or may analyze image data at a timing of generating display data. Also, image data may be analyzed by the server 40 that generates display data or may be analyzed by a device (such as for example an application server) other than the server 40. Also, while information of the number and density of the cells included in biological samples has been exemplified as an example of an analysis result of image data, analysis results are not limited to this.

Also, while an example in which image data is stored in the storage 43 of the server 40 has been described, the server 40 may just store image data in the memory 42 temporarily. Image data generated by the image data generation device 20 may be stored in a device (such as for example a database server) other than the server 40 in a non-volatile manner, and the server 40 may generate display data by reading image data from a device other than the server 40.

Also, while an example in which display data is generated in response to a request from a client terminal that is different from the server 40 has been exemplified, the server 40 may operate as a client terminal. Specifically, the server 40 may generate display data in response to a request from a web browser installed in the server 40 so that the display device, such as a liquid crystal display device etc., connected to the server 40 displays information on the basis of the display data.

Also, while an example has been given in which a plurality of pieces of sample information are aligned and displayed in the vertical direction, the alignment direction is not limited to the vertical direction. It is sufficient if a plurality of pieces of sample information are aligned in a fixed direction, and they may be aligned in the horizontal direction. In such a case, an arbitrary piece of sample information may be confirmed through a scrolling operation in the horizontal direction.

Also, while an example in which the display control system 1 is a web system has been described, the display control system 1 does not have to be a web system but may be a client server system.

What is claimed is:

1. A display control system comprising:
    an image data generation device configured to pick up images of a plurality of samples held in a plurality of holding units so as to generate a plurality of pieces of image data;
    a storage device configured to store the plurality of pieces of image data generated by the image data generation device and a plurality of pieces of position data of holding units corresponding to the plurality of pieces of image data, each of the plurality of pieces of image data being associated with a piece of position data among the plurality of pieces of position data; and
    a display data generation device configured to generate display data based on the plurality of pieces of image data stored in the storage device and the plurality of pieces of position data stored in association with the plurality of pieces of image data,
    wherein the display data comprises:
        data for aligning and displaying, in a fixed direction, a plurality of pieces of sample information each including at least one of (i) one piece of image data, from among the plurality of pieces of image data stored in the storage device, of one of the plurality of samples and (ii) an analysis result on the one piece of image data,
        data for arranging a first piece of sample information and a first piece of position information in such a manner that, while a display device is displaying the first piece of sample information from among the plurality of pieces of sample information based on the display data, the first piece of position information, which graphically identifies a position of a first holding unit corresponding to the first piece of sample information from among the plurality of holding units, is also displayed on the display device, and
        data which enables the plurality of pieces of sample information aligned and displayed in the fixed direction to be movable along the fixed direction in response to a scrolling operation.

2. The display control system according to claim 1, wherein the first piece of position information comprises information indicating a relative position of the first holding unit with respect to others of the plurality of holding units.

3. The display control system according to claim 2, wherein the first piece of position information includes:
    array information that graphically represents an array of the plurality of holding units, and
    identification information that indicates the position of the first holding unit in the array.

4. The display control system according to claim 3, wherein the array information includes a plurality of figures, each of the plurality of figures representing a shape of a holding unit among the plurality of holding units.

5. The display control system according to claim 2, wherein the first piece of position information includes character information that indicates the position of the first holding unit in an array of the plurality of holding units.

6. The display control system according to claim 1, wherein the display data comprises data for aligning and displaying, in the fixed direction, a plurality of pieces of position information corresponding to the plurality of pieces of sample information.

7. The display control system according to claim 2, wherein the display data comprises data for aligning and displaying, in the fixed direction, a plurality of pieces of position information corresponding to the plurality of pieces of sample information.

8. The display control system according to claim 3, wherein the display data comprises data for aligning and displaying, in the fixed direction, a plurality of pieces of position information corresponding to the plurality of pieces of sample information.

9. The display control system according to claim 4, wherein the display data comprises data for aligning and displaying, in the fixed direction, a plurality of pieces of position information corresponding to the plurality of pieces of sample information.

10. The display control system according to claim 5, wherein the display data comprises data for aligning and displaying, in the fixed direction, a plurality of pieces of position information corresponding to the plurality of pieces of sample information.

11. The display control system according to claim 1, wherein the display data generation device is further configured to:
    generate a web page, which is the display data, in response to a request from a client terminal, and
    transmit a response including the web page to the client terminal.

12. A display control method used in a display control system, the display control method comprising:
    picking up, by using an image data generation device included in the display control system, images of a plurality of samples held in a plurality of holding units so as to generate a plurality of pieces of image data;
    storing, by using a storage device included in the display control system, the plurality of pieces of image data generated by the image data generation device and a plurality of pieces of position data of holding units corresponding to the plurality of pieces of image data, each of the plurality of pieces of image data being associated with a piece of position data among the plurality of pieces of position data; and
    generating, by using a display data generation device included in the display control system, display data based on the plurality of pieces of image data stored in the storage device and the plurality of pieces of position data stored in association with the plurality of pieces of image data,
    wherein the display data comprises:
        data for aligning and displaying, in a fixed direction, a plurality of pieces of sample information each including at least one of (i) one piece of image data, from among the plurality of pieces of image data stored in the storage device, of one of the plurality of samples and (ii) an analysis result on the one piece of image data,
        data for arranging a first piece of sample information and a first piece of position information in such a manner that, while a display device is displaying the first piece of sample information from among the plurality of pieces of sample information based on the display data, the first piece of position information, which graphically identifies a position of a first holding unit corresponding to the first piece of sample information from among the plurality of holding units, is also displayed on the display device, and
        data which enables the plurality of pieces of sample information aligned and displayed in the fixed direction to be movable along the fixed direction in response to a scrolling operation.

13. A display control system comprising:
    an image data generation device configured to pick up images of a plurality of samples in a plurality of image pick-up target areas so as to generate a plurality of pieces of image data;
    a storage device configured to store the plurality of pieces of image data generated by the image data generation device and a plurality of pieces of position data of image pick-up target areas corresponding to the plurality of pieces of image data, each of the plurality of pieces of image data being associated with a piece of position data among the plurality of pieces of position data; and
    a display data generation device configured to generate display data based on the plurality of pieces of image data stored in the storage device and the plurality of pieces of position data stored in association with the plurality of pieces of image data,
    wherein the display data comprises:
        data for aligning and displaying, in a fixed direction, a plurality of pieces of sample information each including at least one of (i) one piece of image data, from among the plurality of pieces of image data stored in the storage device, of one of the plurality of samples and (ii) an analysis result on the one piece of image data,
        data for arranging a first piece of sample information and a first piece of position information in such a manner that, while a display device is displaying the first piece of sample information from among the plurality of pieces of sample information based on the display data, the first piece of position information, which graphically identifies a position of a first image pick-up target area corresponding to the first piece of sample information from among the image pick-up target areas, is also displayed on the display device, and
        data which enables the plurality of pieces of sample information aligned and displayed in the fixed direction to be movable along the fixed direction in response to a scrolling operation.

14. The display control system according to claim 13, wherein the first piece of position information comprises information indicating a relative position of the first image pick-up target area with respect to others of the plurality of image pick-up target areas.

15. The display control system according to claim 14, wherein the first piece of position information includes:

array information that graphically represents an array of the plurality of image pick-up target areas, and identification information that indicates the position of the first image pick-up target area in the array.

16. The display control system according to claim 15, wherein the array information includes a plurality of figures, each of the plurality of figures representing a shape of an image pick-up target area among the plurality of image pick-up target areas.

17. The display control system according to claim 14, wherein the first piece of position information includes character information that indicates the position of the first image pick-up target area in an array of the plurality of image pick-up target areas.

18. The display control system according to claim 13, wherein the display data comprises data for aligning and displaying, in the fixed direction, a plurality of pieces of position information corresponding to the plurality of pieces of sample information.

19. The display control system according to claim 13, wherein the display data generation device is further configured to:

generate a web page, which is the display data, in response to a request from a client terminal, and transmit a response including the web page to the client terminal.

20. A display control method used in a display control system, the display control method comprising:

picking up, by using an image data generation device included in the display control system, images of a plurality of samples held in a plurality of image pick-up target areas so as to generate a plurality of pieces of image data;

storing, by using a storage device included in the display control system, the plurality of pieces of image data generated by the image data generation device and a plurality of pieces of position data of image pick-up target areas corresponding to the plurality of pieces of image data, each of the plurality of pieces of image data being associated with a piece of position data among the plurality of pieces of position data; and generating, by using a display data generation device included in the display control system, display data based on the plurality of pieces of image data stored in the storage device and the plurality of pieces of position data stored in association with the plurality of pieces of image data, wherein the display data comprises:

data for aligning and displaying, in a fixed direction, a plurality of pieces of sample information each including at least one of (i) one piece of image data, from among the plurality of pieces of image data stored in the storage device, of one of the plurality of samples and (ii) an analysis result on the one piece of image data, data for arranging a first piece of sample information and a first piece of position information in such a manner that, while a display device is displaying the first piece of sample information from among the plurality of pieces of sample information based on the display data, the first piece of position information, which graphically identifies a position of a first image pick-up target area corresponding to the first piece of sample information from among the plurality of image pick-up target areas, is also displayed on the display device, and data which enables the plurality of pieces of sample information aligned and displayed in the fixed direction to be movable along the fixed direction in response to a scrolling operation.

* * * * *